US007026298B2

(12) United States Patent
Phillips et al.

(10) Patent No.: US 7,026,298 B2
(45) Date of Patent: Apr. 11, 2006

(54) ORAL REHYDRATION COMPOSITIONS

(75) Inventors: Kenneth M. Phillips, Bexley, OH (US); Amy L. Marchio, Centerburg, OH (US); Paul F. Pollack, Bexley, OH (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/873,751

(22) Filed: Jun. 4, 2001

(65) Prior Publication Data

US 2003/0077333 A1    Apr. 24, 2003

(51) Int. Cl.
*A01N 43/04* (2006.01)
*A01N 59/16* (2006.01)
*A61K 31/70* (2006.01)
*A61K 33/32* (2006.01)

(52) U.S. Cl. .......................... 514/23; 426/72; 426/74; 514/974; 424/641

(58) Field of Classification Search .................. 514/23, 514/53
See application file for complete search history.

(56) References Cited

U.S. PATENT DOCUMENTS

| 5,489,440 A | 2/1996 | Ndife et al. ................ 424/489 |
| 5,733,759 A | 3/1998 | Taylor et al. ............ 435/172.3 |
| 5,869,459 A | 2/1999 | Waite et al. .................... 514/23 |
| 5,985,339 A * | 11/1999 | Kamarei ...................... 426/72 |

OTHER PUBLICATIONS

John Hopkins School of Public Health, Press Release: Zinc Supplements Impotant in Combating Diarrhea, Nov. 27, 2000.*
The Role of Zinc and Vitamini A in Persistent Diarrhea Among Infants and Young Children, Journal of Pediatric Gastroenterology and Nutrition 26:446-453, Apr. 1998, Lippincott-Raven Publishers, Philadelphia, Bhan et al.
Zinc, Diarrhea, and Pneumonia, The Journal of Pediatrics, vol. 135, No. 6: Dec. 1999; 135-661—4, Hambidge, et al.
Zinc and Health: Current Health and Future Directions, Zinc Deficiency, Malnutrition and the Gastrointestinal Tract, Department of Pediatrics, North Shore Long Island Jewish Health System and New York University School of Medicine, Manhasset, NY 11030, American Society for Nutritional Sciences, 2000 1388S-1392S, Wapnir.
Zinc in the Treatment of Diarrhea, Journal of Pediatric Gastorenterology and Nutrition, vol. 25, No. 3 1997; pp. 363-365, Lippincott-Raven Publishers, Philadelphia, Darmon et al.
Zinc and Micronutrient Supplements for Children, Am J Clin Nutri 1998; 68(suppl): 495S-8S, Allen.
The Emerging Roles of Zinc in Infant nutrion, Dvelopment and Infectious Diseases, Black et al; Dietry Zinc Intake in Pediatric Populations, World Feeding Views, vol. 4, No. 4 2000.
Zinc Supplementation in Young Children with Acute Diarrhea in India, New England Journal of Medicine 333:839-844, Sep. 28, 1995, Sazawal et al.
Therapeutic Effect of Oral Zinc in Acute and Persistent Diarrhea in Children in Developing countries: Pooled Analysis of Randomized Controlled Trials, Am J Clin Nutr 2000; 72:1516-22, Bhutta et al.
Enteric Protein Loss and Intestinal Permeability Changes in Children During Acute Shigellosis and After Recovery: Effect of Zinc Supplementation, Gut, vol. 35, 1707-1711, 1994.
Zinc Supplementation During Diarrhoea, a Fortification Against Mulnutrition?, The Lancet, Aug. 18, 2000 442-443, Behrens et al.
Randomised Controlled Trial of Zinc Supplementation in Malnourished Bangladeshi Children With Acute Diarrhoea, Archieves of Disease in Childhood 1997: 77:196-200; Roy et al.
Zinc Supplementation in Malnourished Children With Persistent Diarrhea in Pakistan, Pediatrics vol. 103 No. 4, Apr. 1999, Bhutta et al.
Zinc Metabolism in Malabsorption Syndromes, Journal of the American College of Nutriton 4:49-64 (1985), McClain.
Therapeutic and preventive effects of zinc on serious childhood infectious diseases in developing countries, Am J Clin Nutr 1998; 68 (suppl): 475S-9S, Black.
Recent Advances in Research on Zinc and Child Health in Developing Countries, Indian Pediatrics, vol. 35, Dec. 1998 pp 1173-1176, Brooks et al.
Increased diarrhoeal and respiratory morbidity in association with Zinc deficiency—a preliminary report, Acta Paediatr 85:148-50, 1996, Bhandari et al.

(Continued)

*Primary Examiner*—James O. Wilson
*Assistant Examiner*—Traviss C. McIntosh, III
(74) *Attorney, Agent, or Firm*—William J. Winter

(57) ABSTRACT

The present invention is directed to a zinc supplemented ORS and its use in the treatment of diarrhea.

15 Claims, No Drawings

OTHER PUBLICATIONS

Double-blind, randomized, controlled trial of zinc or vitamin A supplement in young children with acute diarrhoea, Acta Paediatr 88: 154-60, 1999, Faruque et al.

A Controlled Trial on Utility of Oral Supplementation in Acute Dehydrating Diarrhea in Infants, Journal of Pediatric Gastroenterology and Nutrition 7:877-881 1988, Sachdev et al.

Impact of Zinc Supplementation on Intestinal Permeability in Bangladeshi Children with Acute Diarrhoea and Persistent Diarrhoea Syndrome, Journal of Pediatric Gastroenterology and Nutrition 15: 289-296 1992, Roy et al.

Zinc in the Management of Diarrhea in Young Children, The New England Journal of Medicine, Sep. 28, 1995, vol. 333, No. 13, Penny et al..

Impact of Zinc Supplemetation on Morbidity From Diarrhea and Respiratory Infections Among Rural Guatemalan Children, Pediatrics vol. 99 No. 6, Jun. 1997 pp 808-813, Ruel et al.

Randomized, community-based trial of the effect of zinc supplementation, with and without other micronutrients, on the duration of persistent chldhood diarrhea in Lima, Peru, The Journal of Pediatrics, Aug. 1999, pp 208-217, Penny et al.

Possibilities for zinc in the treatment of acute diarrhea, Am J Clin Nutri 1998; 68(suppl):480S-3S, Fuchs.

Efficacy of zinc supplementation in reducing the incidence and prevalence of acute diarrhea—a community-based, double-blind, controllled trail, Am J Clin Nutr 197; 66:413-8, Sazawal et al, 1996.

Prevention of diarrhea and pneumonia by zinc supplementation in children in developing countries: Pooled analysis of randomized controlled trials, The Journal of Pediatrics, Dec. 1999, pp689-697, Bhutta et al.

Fecal Excretion of Endogenous Zinc During Oral Rehydration Therapy for Acute Diarrhea: Nutritional Implications, The Journal of Trace Elements in Experimental Medicine 7:89-100 (1995), Ruz et al.

Trace mineral balace during acute diarrhea in infants, The Journal of Pediatrics, Sep. 1988, vol. 113 No. 3, pp452-457.

Mineral Excretion during Acut, Dehydrating Diarrhea Treated with Oral Rehydration Therapy, Pediatric Research, vol. 27, No. 2 1990 p 170-175, Ruz et al.

Zinc and diarrhea, Act Paediat Suppl 381-82-6, 1992, Hambidge.

Protracted Diarrhoea: Secondary Monosaccharide Malabsorption and Zinc Deficiency with Cutaneous manifestations During Total Parenteral Nutrition, Eur J. Pediatr. 135, 175-180 (1980), Stern et al.

The Role of Copper, Molybdenum, Selenium, and Zinc in Nutrition and Health, Toxicology, vol. 18 No. 4, Dec. 1998, pp673-685, Chan et al.

* cited by examiner

ORAL REHYDRATION COMPOSITIONS

The present invention is directed to zinc supplemented oral rehydration solutions (ORS) and their use in the management of diarrhea. Others aspects of the invention are directed to gelled ORS's, containing zinc, and their use in the management of diarrhea. Further embodiments are directed to frozen dosage forms of this ORS, such as popsicles.

BACKGROUND

While diarrhea is typically considered a temporary nuisance in western countries, it is a significant cause of morbidity and mortality in the third world. In developing countries, diarrhea is the largest single cause of death among infants and children. Fluid and weight loss from diarrhea can result in severe dehydration, electrolyte imbalance, and acid-base disturbances. If left untreated, these imbalances can lead to death.

Oral rehydration solutions (ORS) are now routinely utilized throughout the world to correct the fluid and electrolyte losses associated with diarrhea. They have significantly decreased the mortality rate in third world children.

ORS contains at a minimum, water, glucose, and sodium. The principle underlying oral rehydration is the phenomenon of coupled transport. The presence of glucose in the ORS increases the absorption of sodium by the body. Every glucose molecule that crosses the intestinal epithelium brings a sodium ion with it, raising the concentration of ions in the blood stream and pulling water out of the gut. The exact concentration of glucose in the oral fluid is very important. Sodium absorption improves as the glucose concentration of the oral fluid is increased up to about 2.5% w/w. At higher concentrations, the glucose can no longer be efficiently absorbed leading to a net reduction in sodium and water absorption. In fact, higher concentrations of glucose increase the osmotic load in the gut, which pulls water out of the blood stream. This leads to a net loss of fluids and electrolytes further exacerbatin dehydration.

The World Health Organization recommends that an ORS contain 90 mEq of sodium per liter, 20 mEq of potassium per liter, 30 mEq carbonate per liter and 111 mM of glucose per liter. Other ORS's containing lower amounts of sodium have been demonstrated to be equally effective. For example, the American Academy of Pediatrics Committee on Nutrition recommendation for ORS is 40–60 mEq/L sodium, 20 mEq/L potassium, and 2.0–2.5 wt./wt. % carbohydrate.

Despite the reduction in mortality that has been associated with ORS, research continues regarding means to further ameliorate the incidence and/or duration of diarrhea. Part of this research has focused upon the role of zinc in diarrhea. Sazawal et al evaluated the impact of zinc supplementation in young children with diarrhea, New England Journal of Medicine,333:839–844 (1995). Sazawal evaluated the impact of zinc supplementation in a double blinded protocol involving 937 children, between the ages of 6 and 35 months. The authors reported that the group receiving zinc supplementation had a clinically significant reduction in both the duration and severity of diarrhea. Zinc supplementation was provided as part of a liquid daily multiple vitamin. All participants were allowed to consume ORS on a prn basis, if they had diarrhea.

A number of studies have been carried out evaluating the role of zinc in diarrhea. World Feeding Views, Volume 4, Number 1, (2000), at page 18, summarizes the results of 8 pediatric clinical studies involving zinc and diarrhea. Seven out of the eight studies report that zinc had beneficial effects on diarrhea. Various investigators observed a reduction in the duration of the diarrhea, a reduction in the number of watery stools, a reduction in stool output, and a reduction in the incidence. All participants were allowed to consume standard ORS solution as needed. Zinc supplementation was supplied separately from the ORS, typically as part of a vitamin regimen.

In view of the benefits which zinc supplementation has provided in the studies cited above, it would appear logical to incorporate zinc into ORS therapy. However, authors have expressed caution against such a strategy. Darmon et al discussed such a proposed ORS in journal of Pediatric Gastro-enterology and Nutrition 25: 363–365 (1997). Darmon et al, at page 364, $2^{nd}$ column, points out that zinc inhibits the intestinal absorption of glucose. Since ORS therapy is based on an active transport mechanism, zinc might actually diminish the net absorption of sodium and water, leading to an ORS having decreased efficacy.

Another potential problem with zinc relates to its taste. The unpleasant taste of zinc is well documented in the literature regarding the use of zinc in treating the common cold. While zinc's impact on the common cold may be controversial, the negative metallic taste associated with zinc is not. For example, refer to Marshall's review of the use of zinc in Canadian Family Physician, 44:1037–1042 (1998.) Bad taste was a commonly observed complaint among participants.

Taste is an important factor in the rate of compliance with ORS, especially in children. The concentration of glucose in ORS is too low to mask the salty taste. Many children object to this taste and refuse to consume the ORS, even if the ORS is flavored. At the initiation of the research leading to this invention, the inventors believed that zinc would significantly decrease the palatability of the ORS and further exacerbate compliance issues, especially in a juvenile population.

The inventors belief is underscored by others knowledgeable in the field. U.S. Pat. No. 5,869,459, Waite et al, addresses the problem of pediatric compliance with ORS therapy. At column 3, line 8, Waite et al states that electrolytes generally have a disagreeable taste. The electrolytes create an unpleasant taste sensation, creating difficulties in getting young children to consume ORS's, despite their diarrhea.

SUMMARY OF THE INVENTION

In accordance with the present invention, it has been discovered that zinc may be incorporated into oral rehydration solutions (ORS). It has surprisingly been discovered that zinc does not adversely affect the flavor of the ORS. In fact, it is often difficult to differentiate zinc supplemented ORS from conventional ORS in sensory testing. Such a result was entirely unexpected.

It has been discovered that the citrate contained within ORS is responsible for blocking the metallic taste associated with zinc. Citrate is normally present in an ORS in order to prevent pH imbalances in a patient. The inventors have surprisingly discovered that citric ions will also blunt the objectionable flavor associated with zinc, even in an unflavored ORS.

Further, the inventors have discovered that zinc does not adversely impact the absorption of glucose as suggested by Darmon et al, supra. The zinc supplemented ORS will provide the benefits described by the World Feeding Views, supra. This dosage form enhances patient convenience.

The ORS of this invention will be similar to those recommended by the WHO. The only significant distinction will be the presence of zinc. The quantity of zinc contained within the ORS can vary widely. However, as a general guideline, the zinc will typically be present in a quantity of from about 0.3 mEq to about 95 mEq per liter, and more typically from about 0.6 mEq to about 5 mEq per liter.

The remaining ingredients within the ORS will be those recommended by the WHO. This specifically includes sodium, potassium, and glucose. A source of citrate ions is incorporated into the ORS due to its impact on the metallic taste associated with zinc. The quantities utilized will be similar to WHO guidelines.

Oral rehydration solutions can be administered in a variety of forms, as is known to those skilled in the art. They can be administered as solutions, flavored or unflavored. They can be administered as gels. They can also be administered as frozen Popsicles, etc. The zinc supplemented ORS's of this invention can be administered in any of these forms.

DETAILED DESCRIPTION OF THE INVENTION

As used herein:
  a) one milliequivalent (mEq) refers to the number of ions in solution as determined by their concentration in a given volume. This measure is expressed as the number of milliequivalents per liter (mEq/L). Milliequivalents may be converted to milligrams by multiplying mEq by the atomic weight of the mineral and then dividing that number by the valence of the mineral.
  b) "ORS" or "ORS's" refers to oral rehydration solution(s).

In addition to zinc, the ORS of this invention contains all the necessary electrolytes and levels thereof required by the Food and Drug Administration for oral rehydration formulations sold in the United States. In addition to sodium (Na+), potassium (K+), chloride (Cl−) and citrate ions, the ORS contains a source of carbohydrate, such as glucose, fructose, or dextrose. Typically, the ORS of this invention comprises water, carbohydrate, zinc ions, sodium ions, potassium ions, chloride ions, and citrate ions.

The quantity of zinc used in the ORS of this invention can vary widely. The goal is to provide sufficient zinc to replace the zinc lost due to the underlying diarrhea and/or vomiting. Incorporating from about 0.3 mEq to about 95 mEq of zinc per liter of ORS will typically accomplish this result. Typically, the ORS will contain from about 0.6 mEq to about 3 mEq of zinc per liter. Alternatively, it may contain from about 0.6 mEq to about 1.2 mEq of zinc per liter. The source of zinc ions is not critical. Any zinc salt suitable for human consumption may be used in the ORS of this invention. Examples of suitable zinc sources include zinc gluconate, zinc sulfate, zinc chloride, zinc citrate, zinc bicarbonate, zinc carbonate, zinc hydroxide, zinc lactate, zinc acetate, zinc fluoride, zinc bromide, and zinc sulfonate.

The quantity of sodium ions used in the ORS can vary widely, as is known to those skilled in the art. Typically, the ORS will contain from about 30 mEq/L to about 95 mEq/L of sodium. In a further embodiment, sodium content can vary from about 30 mEq/L to about 70 mEq/, most preferably from about 40 mEq/L to about 60 mEq/L. Suitable sodium sources include but are not limited to sodium chloride, sodium citrate, sodium bicarbonate, sodium carbonate, sodium hydroxide, and mixtures thereof The ORS will also contain a source of potassium ions. The quantity of potassium can vary widely. However, as a general guideline, the ORS will typically contain from about 10 mEq/L to about 30 mEq/L of potassium. In a further embodiment, it may contain from about 15 mEq/L to about 25 mEq/L of potassium. Suitable potassium sources include but are not limited to, potassium citrate, potassium chloride, potassium bicarbonate, potassium carbonate, potassium hydroxide, and mixtures thereof.

The ORS will also contain a source of carbohydrate. The quantity of carbohydrate utilized is important as described above. The quantity must be maintained at less than about 3% w/w, and more preferably about 2.5% w/w. Quantities ranging from about 3% w/w to about 2.0% w/w are suitable. Excessive carbohydrate will exacerbate the fluid and electrolyte losses associated with diarrhea.

Any carbohydrate used in prior art oral rehydration solutions may be used to practice the present invention. Suitable carbohydrates include, but are not limited to, simple and complex carbohydrates, glucose, dextrose, fructooligosaccharides, fructose and glucose polymers, corn syrup, high fructose corn syrup, sucrose, maltodextrin, and mixtures thereof.

The ORS will also typically include a source of base to replace diarrheal losses. Typically citrate will be incorporated into the ORS to accomplish this result. Citrate is metabolized to an equivalent amount of bicarbonate, the base in the blood that helps maintain acid-base balance. Citrate has the further benefit of masking the metallic taste of zinc as described above. While citrate is the preferred source of base, any base routinely incorporated into rehydration solutions may be used in the practice of the present invention.

The quantity of citrate can vary as is known in the art. Typically, the citrate content ranges from about 10 mEq/L to about 40 mEq/L, more preferably from about 20 mEq/L to about 40 mEq/L, and most preferably from about 25 mEq/L to about 35 mEq/L. Suitable citrate sources include, but are not limited to, potassium citrate, sodium citrate, citric acid and mixtures thereof.

The ORS will also typically contain a source of chloride. The quantity of chloride can vary as is known in the art. Typically the ORS will contain chloride in the amount of from about 30 mEq/L to about 80 mEq/L, more preferably from about 30 mEq/L to about 75 mEq/L, and most preferably from about 30 mEq/L to about 70 mEq/L. Suitable chloride sources include but are not limited to, sodium chloride, potassium chloride and mixtures thereof.

Optionally, indigestible oligosaccharides may be incorporated into the ORS. Indigestible oligosaccharides have a beneficial impact on the microbial flora of the GI tract. They help to suppress the growth of pathogenic organisms such as *Clostridium difficile*. These oligosaccharides selectively promote the growth of a nonpathogenic microbial flora. Such ORS's have been described in U.S. Pat. No. 5,733,759, filed Apr. 5, 1995, the contents of which are hereby incorporated by reference.

Typically, the oligosaccharide will be a fructoologosaccharide, an inulin such as raftilose, or a xylooligosaccharide. The quantity can vary widely, but may range from 1 to 100 grams per liter, and more typically from 3 to 30 grams per liter of ORS.

The ORS of the present invention will also typically include a flavor to enhance its palatability, especially in a pediatric population. The flavor should mask the salty notes of the ORS. Useful flavorings include, but are not limited to, cherry, orange, grape, fruit punch, bubble gum, apple, raspberry and strawberry. Artificial sweeteners may be added to complement the flavor and mask the salty taste. Useful artificial sweeteners include saccharin, nutrasweet, sucralose, acesulfane-K (ace-K), etc.

Preservatives may be added to help extend shelf life. Persons knowledgeable in the art would be able to select the appropriate preservative, in the proper amount, to accomplish this result. Typical preservatives include, but are not limited to, potassium sorbate and sodium benzoate.

In addition to the carbohydrate described above, the ORS may also contain rice flour, or any other component of rice that is beneficial in the treatment of diarrhea. Numerous rice supplemented ORS's have been described in the literature. Methods for using such rice supplemented ORS's are well known to those skilled in the art. Examples of such rice supplemented ORS's include those described in U.S. Pat. No. 5,489,440 issued Feb. 6, 1996; the contents of which are hereby incorporated by reference.

The ORS of this invention can be manufactured using techniques well known to those skilled in the art. As a general guideline, all the ingredients may be dry blended together; dispersed in water with agitation; and optionally heated to the appropriate temperature to dissolve all the constituents. The ORS is then packaged and sterilized to food grade standards as is known in the art.

ORS may be administered in different forms, depending upon patient preference, as is known in the art. For example, some children will consume ORS more readily if it is frozen, like a Popsicle. ORS Popsicles are described in detail in U.S. Pat. No. 5,869,459, the contents of which are hereby incorporated by reference. The ORS of this solution may be administered as frozen Popsicles if the patient desires such a choice.

ORS's have also been formed into gels in order to enhance patient compliance, especially in a pediatric population. The zinc supplemented ORS of this invention may be gelled if desired. Gelled rehydration compositions are described in U.S. patent application Ser. No. 09/368,388 filed Aug. 4, 1999, the contents of which are hereby incorporated by reference. These gels have also been described in PCT Application Ser. No. 99/15862.

As a general overview, the ORS may be formed into a flowable gel. Alternatively, it may also be formed into a self-supporting gel structure. Such a result may be accomplished by incorporating suitable gelling agents into the ORS.

Suitable gelling agents include but are not limited to agar, alginic acid and salts, gum arabic, gum acacia, gum talha, cellulose derivatives, curdlan, fermentation gums, furcellaran, gelatin, gellan gum, gum ghatti, guar gum, iota carrageenan, irish moss, kappa carrageenan, konjac flour, gum karaya, lambda carrageenan, larch gum/arabinogalactan, locust bean gum, pectin, tamarind seed gum, tara gum, gum tragacanth, native and modified starch, xanthan gum and mixtures thereof. Usage rates of said gelling agents range from about 0.05 to about 50 wt./wt. %

Any reference to a numerical range in this application should be considered as being modified by the adjective "about". Further, any numerical range should be considered to provide support for a claim directed to a subset of that range. For example, a disclosure of a range of from 1 to 10 should be considered to provide support in the specification and claims to any subset in that range (i.e. ranges of 2–9, 3–6, 4–5, 2.2–3.6, 2.1 –9.9,etc.). Any reference in the specification or claims to a quantity of an electrolyte should be construed as referring to the final concentration of the electrolyte in the ORS. Tap water often contains residual sodium, chlorine, etc. A value of 40 mEq of sodium, in this application, means that the total sodium present in the ORS equals 40 mEq, taking into account both added sodium as well as the sodium present in the water used to manufacture the ORS. This holds true for all electrolytes including zinc.

The following Examples are being presented in order to further illustrate the invention. However, they should not be construed as limiting the scope of the claims in any manner.

EXAMPLE I

The following example explains how to manufacture a ready-to-drink zinc supplemented rehydration solution. The ORS had the composition outlined in Table I.

TABLE I

| Ingredient | Quantity per 1,000 lb. |
|---|---|
| Water | 963.078 lb. |
| Dextrose, Monohydrate | 22.400 lb. |
| Fructose | 5.200 lb. |
| Citric Acid | 2.700 lb. |
| Sodium Chloride | 2.064 lb. |
| Potassium Citrate | 2.301 lb. |
| Sodium Citrate | 492.0 g |
| Fruit Flavor | 226.8 g |
| Zinc Gluconate | 80.62 g |
| Sucralose | 179.2 g |
| Acesulfame Potassium | 38.1 g |
| Yellow #6 | 7.2 g |

Weigh out the required amount of filtered water and add to blend tank. Heat the water to 110–130° F., with moderate agitation. While maintaining moderate agitation, add the required amount of dextrose. Agitate until dissolved. Add the required amount of fructose. Agitate until dissolved. Add the required amount of the following ingredients, in the order listed, to the dextrose/fructose blend and agitate until dissolved: zinc gluconate, sodium citrate, sodium chloride, potassium citrate, and citric acid. Add the required amount of sucralose (distributred by McNeil Speciality Products Company of New Brunswick, N.J.) and acesulfame potassium (distributed as Sunsett® by Hoechst Food Ingredients of Somerset, N.J.) and agitate until dissolved. Add the yellow #6 and the fruit punch flavor to the batch until dissolved. Cool the blend to 34–45° F. and hold with low agitation. Fill the required number of one liter plastic bottles, apply the foil heat seal to the bottle opening, and retort to food grade sterility standards.

EXAMPLE II

This Example illustrates the preparation ready-to-drink ORS that is packaged in single serving 8 oz bottles. The ORS has the composition outlined in Table II.

TABLE II

| Ingredient | Quantity per 1,000 lbs |
|---|---|
| Water | 964.907 lb. |
| Dextrose, Anhydrous | 20.402 lb. |
| Fructose | 5.100 lb. |
| Citric Acid | 2.994 lb. |
| Sodium Chloride | 2.109 lb. |
| Potassium Citrate | 1.899 lb. |
| Sodium Citrate | 289.6 g |
| Artificial Cherry Flavor | 226.8 g |
| Potassium Sorbate | 226.8 g |
| Sodium Benzoate | 226.8 g |

TABLE II-continued

| Ingredient | Quantity per 1,000 lbs |
|---|---|
| Zinc Gluconate | 80.62 g |
| Sucralose | 53.78 g |
| Acesulfame Potassium | 38.1 g |
| FD&C Red No. 40 | 7.2 g |

Dryblend the amount of the following ingredients as listed in Table II: dextrose, fructose, citric acid, potassium citrate, sodium chloride, sucralose (distributed by McNeil Speciality Products Company of New Brunswick, N.J.), cherry flavor, sodium citrate, potassium sorbate, red #40, sodium benzoate, acesulfame potassium (distributed as Sunett® by Hoechst Food Ingredients of Somerset, N.J.), and zinc gluconate.

Weigh out the specified amount of filtered water and add to a blend tank. Heat the water to 110–130° F., with moderate agitation. While maintaining moderate agitation, add the required amount of the dryblend. Agitate to dissolve. Sterilize the ORS to food grade sterility standards and package into 8 oz bottles.

EXAMPLE III

This Example illustrates how to manufacture a zinc supplemented ORS that will be filled into Popsicle sleeves to enhance pediatric compliance. The ORS had the composition listed in Table III.

TABLE III

| Ingredient | Quantity per 1,000 lb. |
|---|---|
| Water | 960.205 lb. |
| Dextrose, Anhydrous | 25.508 lb |
| Citric Acid | 6.241 lb. |
| Sodium Chloride | 2.109 lb. |
| CMC | 899.922 g |
| Potassium Citrate | 846.256 g |
| Orange Flavor | 226.800 g |
| Potassium Sorbate | 226.800 g |
| Sodium Benzoate | 226.800 g |
| Sucralose | 89.80 g |
| Zinc Gluconate | 80.62 g |
| Acesulfame Potassium | 67.2 g |
| FD&C Yellow No. 6 | 4.5 g |
| FD&C Red No. 40 | 0.5 g |

Dryblend the amount of the following ingredients as listed in Table III dextrose, citric acid, potassium citrate, sodium chloride, sucralose (distributed by McNeil Speciality Products Company of New Brunswick, N.J.), cherry flavor, sodium citrate, potassium sorbate, yellow #6, red #40, sodium benzoate, acesulfame potassium (distributed as Sunett® by Hoechst Food Ingredients of Somerset, N.J.), and zinc gluconate.

Weigh out the required amount of filtered water and add to a blend tank. Heat the water to 110–130° F., with moderate agitation. While maintaining moderate agitiation, add the specified amount of CMC. Agitate to for a minimum of 10 minutes. After 10 minutes of agitation, ensure the CMC is completely dissolved. Add the specified amount of the dryblend. Agitate to dissolve. Sterilize the ORS to food grade sterility standards and package into popsicle sleeves.

EXAMPLE IV

The following Example illustrates the manufacture of a gelled ORS containing zinc. Table IV presents a bill of materials for manufacturing 45.4 kg of an electrolyte gel. A detailed description of its manufacture follows.

TABLE IV

Bill of Materials

| Ingredient | 0.3% Gelcarin |
|---|---|
| Water (gm) | 43,454 |
| Gelcarin ® DG 654B (gm) | 136 |
| Dextrose (gm) | 925 |
| Fructose (gm) | 231 |
| Sodium chloride (gm) | 97.1 |
| Sodium citrate (gm) | 51.2 |
| Potassium citrate (gm) | 96.7 |
| Citric acid (gm) | 122 |
| Aspartame (gm) | 7.48 |
| Acesulfaine K (gm) | 3.86 |
| Cherry flavor (gm) | 227 |
| Zinc Gluconate | 8 gm |
| FD&C Red #40 (gm) | 0.45 |
| Potassium sorbate (gm) | 0 |
| Sodium benzoate (gm) | 0 |

Weigh out the required amount of filtered water and add to a blend tank. Dry blend the required amount of gelling agent, Gelcarin® DG 654B (Gelcarin® DG 654B is a carrageenan, locust bean gum, potassium citrate blend distributed by FMC Philadelphia, Pa.) with the required amount of dextrose. Hereinafter, Gelcarin refers to Gelcarin® DB 654B. Very slowly add the Gelcarin/dextrose mixture while agitation very rapidly. Turn on the steam and heat the water to 170–180° F. Dry blend the required amount of color with some of the fructose and set aside. Add the remaining fructose. Agitate until the fructose is dissolved. Add the required amount of sodium chloride, zinc gluconate, sodium citrate, and potassium citrate. Agitate until the minerals are dissolved. Add the required amount of citric acid. Agitate until the citric acid is dissolved. Add the required amount of artificial sweeteners Aspartame (distributed as NutraSweet® by The NutraSweet Company of Chicago, Ill.) and Acesulfame K (distributed as Sunett® by Hoechst Food Ingredients of Somerset, N.J.). Agitate until the sweeteners are dissolved. Add the required amount of flavor and fructose/color mixture. Agitate until dissolved. Add the required amount of preservatives under agitation until dissolved. Hold the finished blend a minimum of 10 minutes but not more than 2 hours.

The processing does not involve dearation, emulsification or homogenization. Heat the mix through the preheater to 155–165° F. Heat the mix through tubular heater to 230–232° F. and hold for 5 seconds. Cool the mix to 155–165° F. Further cool the mix to 130–232° F. Do not hold the blend more than 2 hours before filling.

The batch may be hot filled or aseptically filled into the desired container. The target filling temperature is 110–120° F. The temperature must not fall below 100° F. or the gel will not set.

EXAMPLE V

Research and Development requested descriptive data to support the evaluation of adding zinc to oral rehydration solution. Sensory Evaluation conducted profile Attribute Analysis (PAA) with the data being statistically analyzed to support this project. Statistical computations were done on SAS® version 8.0 statistical software, SAS Institute, Inc., Cary N.C. A statistical screening design was developed to determine the sample order and combinations of added ingredients prior to evaluation. A total of 32 samples were evaluated. Zinc sources included zinc gluconate and zinc sulfate powders. Added ingredients included carbohydrates (dextrose and fructose), electrolyte sources (sodium chloride, sodium citrate, and potassium citrate), artificial sweeteners (Acesulfame Potassium and Sucralose), and acid (citric acid). Evaluated attributes included basic taste sweet, basic taste sour, basic taste salt, basic taste bitter, musty, astringent mouthfeel, and other.

II. Sample Preparation

Preparation and sample evaluation methods were standardized for each taste session. Four samples were evaluated in each PAA session over a two-week period of time. Professionally trained tasters participated in the PAA taste panel session. The zinc source was weighed and added ingredients into 250 mL amber glass bottles with caps. To each bottle, 250 mL odorless/tasteless room temperature water was added and agitated until the ingredients dissolved. Tables containing zinc and added ingredient amounts per 250 mL bottle are attached (Tables V–VI). Samples were prepared at least two hours prior to tasting to ensure ingredient dissolution. Approximately 1 fluid ounce (29 grams) of each sample was poured into a 5 ounce (142 gram) odorless translucent Dixie® cup. Panelists evaluated each sample and assigned a rating using a 1–7 point scale on a ballot containing key attributes (basic taste sweet, basic taste sour, basic taste salt, basic taste bitter, musty, astringency mouthfeel, and other). Panel data is attached for review (Table VII).

III. Conclusion

A. The flavor of the solution containing zinc gluconate was not affected by the addition of varying levels and types of carbohydrate, electrolytes (sodium, potassium), artificial sweeteners, and/or citric acid.

B. The flavor of the solution containing zinc sulfate contained a very slight "musty" note. The impact of the "musty" note was reduced by the addition of artificial sweetener and/or citric acid.

TABLE V

Zinc Gluconate (0.045 g/250 mL)

| Sample (Cup) Code | Carbohydrate | Electrolyte | Artificial Sweetener | Citric Acid |
|---|---|---|---|---|
| 596 | 1.275 g Fructose 5.575 g Dextrose | 0.535 Sodium Chloride 0.2825 Sodium Citrate 0.5925 Potassium Citrate | 0.021 Acesulfame K 0.10 Sucralose | 0.125 |
| 663 | 1.275 g Fructose 5.575 g Dextrose | | 0.021 Acesulfame K 0.10 Sucralose | 0.125 |
| 113 | | 0.535 Sodium Chloride 0.2825 Sodium Citrate 0.5925 Potassium Citrate | | 0.125 |
| 422 | | | | |
| 604 | | | 0.021 Acesulfame K 0.10 Sucralose | 0.125 |
| 463 | | 0.535 Sodium Chloride 0.2825 Sodium Citrate 0.5925 Potassium Citrate | | |
| 222 | 1.275 g Fructose 5.575 g Dextrose | | | 0.125 |
| 533 | 1.275 g Fructose 5.575 g Dextrose | 0.535 Sodium Chloride 0.2825 Sodium Citrate 0.5925 Potassium Citrate | 0.021 Acesulfame K 0.10 Sucralose | |
| 401 | 1.275 g Fructose 5.575 g Dextrose | | | |
| 824 | 1.275 g Fructose 5.575 g Dextrose | 0.535 Sodium Chloride 0.2825 Sodium Citrate 0.5925 Potassium Citrate | | 0.125 |
| 627 | | | 0.021 Acesulfame K 0.10 Sucralose | |
| 329 | | 0.535 Sodium Chloride 0.2825 Sodium Citrate 0.5925 Potassium Citrate | 0.021 Acesulfame K 0.10 Sucralose | 0.125 |
| 556 | | 0.535 Sodium Chloride 0.2825 Sodium Citrate 0.5925 Potassium Citrate | 0.021 Acesulfame K 0.10 Sucralose | |
| 670 | 1.275 g Fructose 5.575 g Dextrose | | 0.021 Acesulfame K 0.10 Sucralose | 0.125 |
| 459 | 1.275 g Fructose 5.575 g Dextrose | 0.535 Sodium Chloride 0.2825 Sodium Citrate 0.5925 Potassium Citrate | | |
| 261 | | | | 0.125 |

TABLE V1

Zinc Sulfate (0.02375 g/250 mL)

| Sample (Cup) Code | Carbohydrate | Electrolyte | Artificial Sweetener | Citric Acid |
|---|---|---|---|---|
| 710 | 1.275 g Fructose 5.575 g Dextrose | 0.535 Sodium Chloride 0.2825 Sodium Citrate 0.5925 Potassium Citrate | 0.021 Acesulfame K 0.10 Sucralose | 0.125 |
| 250 | 1.275 g Fructose 5.575 g Dextrose | | 0.021 Acesulfame K 0.10 Sucralose | 0.125 |
| 359 | | 0.535 Sodium Chloride 0.2825 Sodium Citrate 0.5925 Potassium Citrate | | 0.125 |
| 530 | | | | |
| 850 | | | 0.021 Acesulfame K 0.10 Sucralose | 0.125 |
| 465 | | 0.535 Sodium Chloride 0.2825 Sodium Citrate 0.5925 Potassium Citrate | | |
| 649 | 1.275 g Fructose 5.575 g Dextrose | | | 0.125 |
| 651 | 1.275 g Fructose 5.575 g Dextrose | 0.535 Sodium Chloride 0.2825 Sodium Citrate 0.5925 Potassium Citrate | 0.021 Acesulfame K 0.10 Sucralose | |
| 678 | 1.275 g Fructose 5.575 g Dextrose | | | |
| 863 | 1.275 g Fructose 5.575 g Dextrose | 0.535 Sodium Chloride 0.2825 Sodium Citrate 0.5925 Potassium Citrate | | 0.125 |
| 716 | | | 0.021 Acesulfame K 0.10 Sucralose | |
| 728 | | 0.535 Sodium Chloride 0.2825 Sodium Citrate 0.5925 Potassium Citrate | 0.021 Acesulfame K 0.10 Sucralose | 0.125 |
| 247 | | 0.535 Sodium Chloride 0.2825 Sodium Citrate 0.5925 Potassium Citrate | 0.021 Acesulfame K 0.10 Sucralose | |
| 570 | 1.275 g Fructose 5.575 g Dextrose | | 0.021 Acesulfame K 0.10 Sucralose | 0.125 |
| 840 | 1.275 g Fructose 5.575 g Dextrose | 0.535 Sodium Chloride 0.2825 Sodium Citrate 0.5925 Potassium Citrate | | |
| 650 | | | | 0.125 |

TABLE VII

Zinc PAA Final Averages

| Sample ID | Date | Sweet | Sour | Salt | Bitter | Musty | Astringent | Other |
|---|---|---|---|---|---|---|---|---|
| 596 | Apr. 23, 2001 | 4.67 | 2.83 | 2.67 | 2.00 | 1.00 | 2.50 | 1.33 |
| 663 | Apr. 23, 2001 | 4.67 | 1.67 | 1.50 | 2.00 | 1.00 | 2.83 | 1.00 |
| 113 | Apr. 23, 2001 | 1.00 | 1.83 | 3.00 | 1.50 | 1.33 | 2.50 | 1.00 |
| 442 | Apr. 23, 2001 | 1.00 | 1.33 | 1.33 | 2.17 | 1.33 | 2.83 | 1.00 |
| 604 | Apr. 24, 2001 | 3.83 | 3.17 | 1.50 | 1.50 | 1.00 | 2.50 | 1.00 |
| 463 | Apr. 24, 2001 | 1.00 | 1.50 | 2.67 | 1.50 | 1.50 | 2.83 | 1.00 |
| 222 | Apr. 24, 2001 | 2.17 | 3.00 | 1.17 | 1.67 | 1.50 | 2.83 | 1.00 |
| 533 | Apr. 24, 2001 | 4.83 | 1.67 | 2.17 | 1.67 | 1.00 | 2.83 | 1.00 |
| 401 | Apr. 24, 2001 | 2.00 | 1.25 | 1.25 | 1.75 | 1.50 | 2.25 | 1.00 |
| 824 | Apr. 24, 2001 | 2.25 | 1.75 | 2.75 | 1.50 | 1.25 | 2.75 | 2.25 |
| 627 | Apr. 24, 2001 | 4.00 | 1.50 | 1.50 | 2.50 | 1.50 | 3.25 | 1.25 |
| 329 | Apr. 24, 2001 | 3.75 | 2.50 | 2.75 | 1.50 | 1.50 | 3.00 | 1.00 |
| 556 | Apr. 25, 2001 | 4.20 | 1.60 | 2.40 | 1.60 | 1.20 | 2.40 | 1.00 |
| 670 | Apr. 25, 2001 | 4.00 | 3.33 | 1.50 | 1.67 | 1.33 | 2.50 | 1.33 |
| 459 | Apr. 25, 2001 | 2.17 | 1.67 | 2.67 | 1.67 | 1.67 | 2.67 | 1.00 |
| 261 | Apr. 25, 2001 | 1.17 | 3.50 | 1.33 | 2.00 | 1.17 | 3.20 | 1.00 |
| 710 | Apr. 25, 2001 | 4.50 | 1.75 | 2.75 | 1.50 | 1.00 | 2.75 | 1.17 |
| 250 | Apr. 25, 2001 | 4.00 | 1.80 | 1.20 | 2.00 | 1.20 | 3.20 | 1.00 |
| 359 | Apr. 25, 2001 | 1.00 | 2.40 | 3.00 | 1.40 | 1.60 | 2.80 | 1.00 |
| 530 | Apr. 25, 2001 | 1.00 | 1.40 | 1.00 | 2.20 | 2.60 | 3.00 | 1.00 |
| 850 | Apr. 26, 2001 | 3.75 | 3.00 | 1.25 | 2.75 | 1.00 | 3.00 | 1.00 |
| 465 | Apr. 26, 2001 | 1.00 | 1.00 | 2.50 | 1.50 | 2.25 | 2.75 | 1.00 |
| 649 | Apr. 26, 2001 | 2.25 | 3.25 | 1.25 | 1.50 | 1.25 | 2.75 | 1.00 |
| 651 | Apr. 26, 2001 | 4.75 | 1.50 | 2.50 | 1.50 | 1.00 | 2.50 | 1.00 |
| 678 | Apr. 26, 2001 | 2.00 | 1.50 | 1.00 | 1.75 | 2.25 | 2.75 | 1.50 |
| 863 | Apr. 26, 2001 | 2.00 | 1.75 | 2.25 | 1.25 | 1.25 | 2.75 | 1.00 |

TABLE VII-continued

Zinc PAA Final Averages

| Sample ID | Date | Sweet | Sour | Salt | Bitter | Musty | Astringent | Other |
|---|---|---|---|---|---|---|---|---|
| 716 | Apr. 26, 2001 | 4.25 | 1.75 | 1.00 | 2.25 | 1.25 | 3.50 | 1.00 |
| 728 | Apr. 26, 2001 | 3.75 | 1.50 | 2.50 | 1.25 | 1.25 | 2.50 | 1.00 |
| 247 | Apr. 27, 2001 | 4.40 | 1.60 | 2.40 | 1.80 | 1.20 | 2.80 | 1.00 |
| 570 | Apr. 27, 2001 | 4.60 | 3.40 | 1.40 | 1.60 | 1.20 | 3.20 | 1.00 |
| 840 | Apr. 27, 2001 | 1.60 | 1.40 | 1.80 | 1.60 | 1.40 | 2.60 | 2.00 |
| 650 | Apr. 27, 2001 | 1.00 | 3.40 | 1.00 | 2.00 | 1.20 | 3.60 | 1.00 |

1 = none
3 = slight
5 = moderate
7 = strong

We claim:

1. A method for providing a zinc-containing aqueous solution with improved palatability for oral rehydration therapy to a patient in need thereof comprising administering to said patient said aqueous solution comprising:
    a. from about 0.3 mEq to about 95 mEq of zinc per liter;
    b. from about 10 mEq to about 40 mEq of citrate per liter;
    c. from about 30 niEq to about 95 mEq of sodium per liter;
    d. from about 10 mEq to about 30 mEq of potassium per liter; and
    e. a carbohydrate,
wherein the carbohydrate is maintained within the composition at less than about 3% w/w.

2. The method according to claim 1 in which said aqueous solution contains chloride.

3. The method according to claim 1 in which said carbohydrate is a mixture of dextrose and fructose.

4. The method according to claim 1 wherein said carbohydrate is present in a quantity of less than about 2.5 wt/wt %.

5. The method according to claim 1 in which said sodium is present in the quantity of about 30 mEq/L to about 70 mEq/L.

6. The method according to claim 1 wherein said sodium is selected from the group consisting of sodium chloride, sodium citrate, sodium bicarbonate, sodium carbonate, sodium hydroxide and mixtures thereof.

7. The method according to claim 1 in which said potassium is present in the quantity of about 15 mEq/L to about 25 mEq/L.

8. The method according to claim 1 wherein said potassium is selected from the group consisting of potassium citrate, potassium chloride, potassium bicarbonate, potassium carbonate, potassium hydroxide and mixtures thereof.

9. The method according to claim 1 in which said zinc is present in the quantity of from about 0.6 mEq/L to about 5 mEq/L.

10. The method according to claim 1 in which said zinc is present in the quantity of from about 0.6 mEq/L to about 1.2 mEq/L.

11. The method according to claim 1 in which said zinc is selected from the group consisting of zinc gluconate, zinc chloride, zinc sulfate, zinc citrate, zinc carbonate, zinc hydroxide, zinc lactate, zinc acetate, zinc fluoride, zinc bromide, and zinc sulfonate.

12. The method according to claim 2 in which said chloride is present in the quantity of from about 30 mEq/L to about 80 mEq/L.

13. The method according to claim 2 in which said chloride is selected from the group consisting of potassium chloride, sodium chloride, and zinc chloride.

14. The method according to claim 1 in which said citrate is present in the quantity of from about 20 mEq/L to about 40 mEq/L.

15. The method according to claim 1 in which the citrate is selected from the group consisting of potassium citrate, sodium citrate, and citric acid.

* * * * *